United States Patent
LaRosa et al.

(10) Patent No.: US 12,285,461 B2
(45) Date of Patent: *Apr. 29, 2025

(54) TOPICAL ANTIBIOTIC

(71) Applicant: Concept Matrix Solutions, Newbury park, CA (US)

(72) Inventors: Tony LaRosa, Woodland Hills, CA (US); Robert Davidson, Woodland Hills, CA (US); David Reid, Woodland Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/186,639

(22) Filed: Mar. 20, 2023

(65) Prior Publication Data

US 2023/0226144 A1 Jul. 20, 2023

Related U.S. Application Data

(63) Continuation of application No. 16/946,990, filed on Jul. 14, 2020, now Pat. No. 11,607,442.

(60) Provisional application No. 62/978,345, filed on Feb. 19, 2020, provisional application No. 62/907,754, filed on Sep. 30, 2019.

(51) Int. Cl.
| | |
|---|---|
| *A61K 31/05* | (2006.01) |
| *A61K 9/00* | (2006.01) |
| *A61K 9/06* | (2006.01) |
| *A61K 31/65* | (2006.01) |
| *A61K 31/702* | (2006.01) |
| *A61K 38/12* | (2006.01) |
| *A61K 45/06* | (2006.01) |
| *A61K 47/06* | (2006.01) |

(52) U.S. Cl.
CPC ............ *A61K 38/12* (2013.01); *A61K 9/0014* (2013.01); *A61K 9/06* (2013.01); *A61K 31/05* (2013.01); *A61K 31/65* (2013.01); *A61K 31/702* (2013.01); *A61K 45/06* (2013.01); *A61K 47/06* (2013.01)

(58) Field of Classification Search
CPC ........ A61K 38/12; A61K 9/0014; A61K 9/06; A61K 31/05; A61K 31/65; A61K 31/702; A61K 45/06; A61K 47/06
See application file for complete search history.

(56) References Cited

U.S. PATENT DOCUMENTS

2019/0247299 A1* 8/2019 Cameron ............... A61K 47/10

OTHER PUBLICATIONS

National Institute of Health (https://www.niaid.nih.gov/research/antimicrobial-resistance-threats Feb. 11, 2020) (Year: 2020).*
CDC (https://www.cdc.gov/fungal/diseases/index.html accessed May 21, 2021) (Year: 2021).*
Doron ("Bacterial infections: Overview"; International Encyclopedia of Public Heatlh, 2008:273-282) (Year: 2008).*
Merck Manual (https://www.merckmanuals.com/home/skin-disorders/fungal-skin-infections/overview-of-fungal-skin-infections accessed Feb. 19, 2019) (Year: 2019).*
Merck Manual—fungal infections overview (https://www.merckmanuals.com/professional/infectious-diseases/fungi/overview-of-fungal-infections accessed Oct. 21, 2020) (Year: 2020).*
Merck Manual (https://www.merckmanuals.com/professional/infectious-diseases/viruses/overview-of-viruses accessed Feb. 19, 2019) ( Year: 2019).*
Merck Manual (https://www.merckmanuals.com/professional/infectious-diseases/approach-to-parasitic-infections/approach-to-parasitic-infections?query=protozoa accessed Oct. 22, 2020 (Year: 2020).*
United States Patent and Trademark Office, "Notice of Allowance and Fee(s) Due", U.S. Appl. No. 16/946,990, filed Nov. 28, 2022, 11 pgs.

* cited by examiner

*Primary Examiner* — Julie Ha
*Assistant Examiner* — Kristina M Hellman
(74) *Attorney, Agent, or Firm* — Carlson, Caspers, Vandenburgh & Lindquist, P.A.

(57) ABSTRACT

Provided herein is a topical antibiotic composition that includes an external antibiotic agent, one or more pharmaceutically acceptable excipients, and at least one of a cannabinoid, terpene, and flavonoid. Also provided is a method that includes topically administering to a skin surface of a subject (e.g., human) the topical antibiotic composition.

13 Claims, No Drawings

TOPICAL ANTIBIOTIC

RELATED U.S. APPLICATION DATA

This application is a continuation patent application of U.S. application Ser. No. 16/946,990, filed Jul. 14, 2020, now U.S. Pat. No. 11,607,442, which claims the benefit of priority to U.S. provisional patent application No. 62/907,754 filed on Sep. 30, 2019, and U.S. provisional patent application No. 62/978,345 filed Feb. 19, 2020, the contents of which are incorporated by reference herein in their entirety.

SUMMARY OF THE INVENTION

The present invention provides for a topical antibiotic composition (e.g., first aid topical antibiotic ointment) that includes (a) at least one of bacitracin, bacitracin zinc, neomycin, neomycin sulfate, tetracycline, tetracycline hydrochloride, and polymyxin b sulfate; (b) at least one of a cannabinoid, terpene, and flavonoid; and (c) one or more pharmaceutically acceptable topical excipients (e.g., solvent, emulsifier, thickening agent, and/or emollient).

The present invention provides for a topical antibiotic composition (e.g., first aid topical antibiotic ointment) that includes (a) at least one of bacitracin, bacitracin zinc, neomycin, neomycin sulfate, tetracycline, tetracycline hydrochloride, and polymyxin b sulfate; (b) at least one of a cannabinoid, terpene, and flavonoid; and (c) at least one of petrolatum, white petrolatum, hard paraffin, liquid paraffin, and white soft paraffin.

The present invention also provides for a method that includes topically administering to a skin surface of a subject (e.g., human at least 2 years of age) the topical composition described herein.

The present invention also provides for a method that includes topically administering to a skin surface of a subject (e.g., human at least 2 years of age) the topical composition described herein to treat, prevent infection, ameliorate, or manage at least one of: (i) minor cuts, (ii) scrapes, (iii) burns.

The present invention also provides for a method that includes topically administering to a skin surface of a subject (e.g., human at least 2 years of age) the topical composition described herein to: prevent infection and for the temporary relief of pain or discomfort due to at least one of minor cuts, scrapes, and burns, in need thereof the topical antibiotic.

DETAILED DESCRIPTION

Compositions of the present invention may be beneficial in preventing, treating, managing, and/or ameliorating a variety of skin wounds. Specifically, the compositions may be beneficial in preventing, treating, managing, and/or ameliorating at least one of: (i) minor cuts, (ii) scrapes, (iii) burns. More specifically, the compositions may be beneficial to prevent infection and for the temporary relief of pain or discomfort due to at least one of minor cuts, scrapes, and burns, in need thereof the topical antibiotic.

The compositions of the present invention include at least one of a cannabinoid, terpene, and flavonoid. Without wishing to be limited to any particular theory, it is currently believed that the cannabinoid, terpene, and/or flavonoid provides stability to the composition, which serves to prevent phase separation of an aqueous and a lipid phase in the composition at elevated temperatures (e.g. temperatures of more than about 25° C.), which might promote improved or prolonged contact to the skin, resulting in the observed increased retention times of the active(s) in the dermis and epidermis.

Across multiple topical dosage forms (e.g., creams, gels, lotions, ointments, foams, etc.) the cannabinoid, terpene, and/or flavonoid can be present in an amount, such that it exhibits activity as an active ingredient for the intended purpose (e.g., minor cuts or scrapes). In doing so, the cannabinoid, terpene, and/or flavonoid may further have a synergistic effect with the active ingredient(s) present therein. In other aspects, the cannabinoid, terpene, and/or flavonoid can be present in sub-therapeutic amounts.

It is currently believed that the topical use of the cannabinoid, terpene, and/or flavonoid provides additional benefits, which include: smoothing skin, strengthening underlying epidermal tissue, removing dead skin cells, balancing oil production, and helping the skin retain moisture levels. It is further believed that the cannabinoid, terpene, and/or flavonoid helps cleanse and moisturize the skin. Healthy skin is just like any other organ in your body: It continuously needs oxygen and nutrients to be brought to the cells, and toxins need to be washed away. It is further believed that the cannabinoid, terpene, and/or flavonoid contributes to the optimal skin health while leaving skin feeling and looking youthful.

It is also currently believed that some consumers have a preference to use a topical skin product that is environmentally friendly to produce and includes fewer toxic chemicals that are otherwise put into the environment when creating topical skin products. Inclusion of substances, such as cannabinoids and terpenes (which are natural products), are viable options for such consumers.

Definitions:

As used herein, "ointment" refers to a homogeneous, viscous, semi-solid preparation, most commonly a greasy, thick oil (oil 80%-water 20%) with a high viscosity, that is intended for external application to the skin or mucous membranes. They are used as emollients or for the application of active ingredients to the skin for protective, therapeutic, or prophylactic purposes and where a degree of occlusion is desired.

Ointments are usually very moisturizing, and good for dry skin. They have a low risk of sensitization due to having few ingredients beyond the base oil or fat, and low irritation risk. The vehicle of an ointment is known as the ointment base. The choice of a base depends upon the clinical indication for the ointment. The different types of ointment bases are:

Hydrocarbon bases, e.g. hard paraffin, soft paraffin, microcrystalline wax and ceresine Absorption bases, e.g. wool fat, beeswax Water-soluble bases, e.g. macrogols 200, 300, 400

Emulsifying bases, e.g. emulsifying wax, cetrimide

Vegetable oils, e.g. olive oil, coconut oil, sesame oil, almond oil and peanut oil.

The medicaments are dispersed in the base and are divided after penetrating the living cells of the skin. Ointments have a water number that can define the maximum amount of water that it can contain. The water number of an ointment is the maximum quantity of water that 100 g of a base can contain at 20° C.

Ointments are typically formulated using hydrophobic, hydrophilic, or water-emulsifying bases to provide preparations that are immiscible, miscible, or emulsifiable with skin secretions. They can also be derived from hydrocarbon (fatty), absorption, water-removable, or water-soluble bases.

The term "topical antibiotic composition" refers to a topical composition containing an external antibiotic agent, various inactive ingredients or excipients, and at least one of a terpene and cannabinoid. The composition is suitable for the prophylactic or therapeutic topical treatment of minor cuts, scrapes or burns.

The term "antibiotic" refers to a medicine or antimicrobial chemical compound that is active against bacteria to prevent or treat bacterial infections by killing bacteria or inhibiting the growth of bacteria.

The term "external antibiotic agent" or "antibiotic agent" refers to any chemical and/or biological agent (e.g., an antimicrobial peptide) that when topically administered at the site of the wounded skin, effectively treats and/or leads to a visible reduction of symptoms associated with the epithelial condition of a minor cut or scrape. Representative antibiotic agents include, for example bacitracin, bacitracin zinc, neomycin, neomycin sulfate, tetracycline, tetracycline hydrochloride, and polymyxin b sulfate.

The term "solvent" refers to a substance, typically a liquid at ambient conditions, capable of dissolving another substance (a solute), resulting in a solution. When one substance is dissolved into another, a solution is formed. This is opposed to the situation when the compounds are insoluble like sand in water. In solution, all of the ingredients are uniformly distributed at a molecular level and no residue remains. The mixing is referred to as miscibility, whereas the ability to dissolve one compound into another is known as solubility. However, in addition to mixing, both substances in the solution interact with each other. When something is dissolved, molecules of the solvent arrange themselves around molecules of the solute. Heat is involved and entropy is increased making the solution more thermodynamically stable than the solute alone. This arrangement is mediated by the respective chemical properties of the solvent and solute, such as hydrogen bonding, dipole moment and polarizability.

The term "emollient" refers to lubricating ingredients (e.g., fats, phospholipids and sterols) that soften and smooth skin while helping it to retain moisture. Emollients are typically nonpolar and can come from natural or synthetic sources in the form of plant oils, mineral oils, shea butter, cocoa butter, petrolatum, cholesterol, silicones or animal oils (including emu, mink and lanolin).

The term "pain relief" refers to a chemical or drug compound added to a topical first aid antibiotic composition to relieve or minimize pain caused by a skin wound (e.g., minor cuts, scrapes, burn). Representative pain relief agents include, for example lidocaine and pramoxine hydrochloride.

The term "infection" refers to the invasion of tissue by microorganisms and pathogens (e.g., bacteria, virus, fungus, and parasite) leading to disease. Wounded skin caused by minor cuts, scrapes or burns opens the skin and exposes underlying tissue and the bloodstream to pathogens. Symptoms or signs of infection include hot incision site, redness and swelling, continual or increased pain, fluid drainage, fever, and malaise.

The term "hemp extract" refers to Cannabidiol (CBD) oil that can be extracted from the stalks, stems and flowers of the *Cannabis sativa* plant, which does not include the seeds of the plant. This oil can be used to dissolve CBD and added into ointments for its helps properties, in which it does not contain any psychoactive properties.

The term "cannabinoid" refers to a class of diverse chemical compounds that act on cannabinoid receptors on cells that repress neurotransmitter release in the brain. These receptor proteins include the endocannabinoids (produced naturally in the body by humans and animals), the phytocannabinoids (found in *Cannabis* and some other plants), and synthetic cannabinoids (manufactured chemically). The most notable cannabinoid is the phytocannabinoid Δ9-tetrahydrocannabinol (THC), the primary psychoactive compound of *Cannabis*. Cannabidiol (CBD) is another major constituent of the plant, representing up to 40% in extracts of the plant resin. There are at least 85 different cannabinoids isolated from *Cannabis*, exhibiting varied effects. The cannabinoid can be synthetically prepared, or alternatively, can be obtained naturally (e.g., from plant matter). Either way, the cannabinoid can have the requisite purity (e.g., at least 95 wt. % pure, at least 98 wt. % pure, at least 99 wt. % pure, or at least 99.5 wt. % pure).

| | Cannabinoids isolated from Cannabis |
|---|---|
| 1. | Cannabigerol ((E)-CBG-C5) |
| 2. | Cannabigerol monomethyl ether ((E)-CBGM-C5 A) |
| 3. | Cannabinerolic acid A ((Z)-CBGA-C5 A) |
| 4. | Cannabigerovarin ((E)-CBGV-C3) |
| 5. | Cannabigerolic acid A ((E)-CBGA-C5 A) |
| 6. | Cannabigerolic acid A monomethyl ether ((E)-CBGAM-C5 A) |
| 7. | Cannabigerovarinic acid A ((E)-CBGVA-C3 A) |
| 8. | (±)-Cannabichromene (CBC-C5) |
| 9. | (+)-Cannabichromenic acid ACBCA-C5 A |
| 10. | (+)-Cannabivarichromene or (+)-Cannabichromevarin (CBCV-C3) |
| 11. | (+)-Cannabichromevarinic acid A (CBCVA-C3 A) |
| 12. | (−)-Cannabidiol (CBD-C5) |
| 13. | Cannabidiol momomethyl ether (CBDM-C5) |
| 14. | Cannabidiol-C4 (CBD-C4) |
| 15. | (−)-Cannabidivarin CBDV-C3 |
| 16. | Cannabidiorcol (CBD-C1) |
| 17. | Cannabidiolic acid (CBDA-C5) |
| 18. | Cannabidivarinic acid (CBDVA-C3) |
| 19. | Cannabinodiol (CBND-C5) |
| 20. | Cannabinodivarin (CBND-C3) |
| 21. | Δ9-Tetrahydrocannabinol (Δ9-THC-C5) |
| 22. | Δ9-Tetrahydrocannabinol-C4 (Δ9-THC-C4) |
| 23. | Δ9-Tetrahydrocannabivarin (Δ9-THCV-C3) |
| 24. | Δ9-Tetrahydrocannabiorcol (Δ9-THCO-C1) |
| 25. | Δ9-Tetrahydro- cannabinolic acid A (Δ9-THCA-C5 A) |
| 26. | Δ9-Tetrahydro- cannabinolic acid B (Δ9-THCA-C5 B) |
| 27. | Δ9-Tetrahydro- cannabinolic acid-C4A and/or B (Δ9-THCA-C4A and/or B) |
| 28. | Δ9-Tetrahydro- cannabivarinic acid A (Δ9-THCVA-C3A) |
| 29. | Δ9-Tetrahydro- cannabiorcolic acid A and/or B (Δ9-THCOA-C1A and/or B) |
| 30. | (−)-Δ8-trans-(6aR,10aR)-Δ8-Tetrahydrocannabinol (Δ8-THC-C5) |
| 31. | (−)-Δ8-trans-(6aR,10aR)- Tetrahydrocannabinolic acid A (Δ8-THCA-C5 A) |
| 32. | (−)-(6aS,10aR)-Δ9-Tetrahydrocannabinol ((−)-cis-Δ9-THC-C5) |
| 33. | Cannabinol (CBN-C5) |
| 34. | Cannabinol-C4 (CBN-C4) |
| 35. | Cannabivarin (CBN-C3) |
| 36. | Cannabinol-C2 (CBN-C2) |
| 37. | Cannabiorcol (CBN-C1) |
| 38. | Cannabinolic acid A (CBNA-C5 A) |
| 39. | Cannabinol methyl ether (CBNM-C5) |
| 40. | (−)-(9R,10R)-trans- Cannabitriol ((−)-trans-CBT-C5) |
| 41. | (+)-(9S,10S)-Cannabitriol ((+)-trans-CBT-C5) |
| 42. | (±)-(9R,10S/9S,10R)- Cannabitriol ((±)-cis-CBT-C5) |
| 43. | (−)-(9R,10R)-trans- 10-O-Ethyl-cannabitriol ((−)-trans-CBT-OEt-C5) |
| 44. | (±)-(9R,10R/9S,10S)- Cannabitriol-C3 ((±)-trans-CBT-C3) |
| 45. | 8,9-Dihydroxy-Δ6a(10a)- tetrahydrocannabinol (8,9-Di-OH-CBT-C5) |
| 46. | Cannabidiolic acid A cannabitriol ester (CBDA-C5 9-OH-CBT-C5 ester) |

| | Cannabinoids isolated from Cannabis |
|---|---|
| 47. | (−)-(6aR,9S,10S,10aR)- 9,10-Dihydroxy-hexahydrocannabinol, Cannabiripsol (Cannabiripsol-C5) |
| 48. | (−)-6a,7,10a-Trihydroxy-Δ9-tetrahydrocannabinol ((−)-Cannabitetrol) |
| 49. | 10-Oxo-Δ6a(10a)- tetrahydrocannabinol (OTHC) |
| 50. | (5aS,6S,9R,9aR)- Cannabielsoin (CBE-C5) |
| 51. | (5aS,6S,9R,9aR)- C3-Cannabielsoin (CBE-C3) |
| 52. | (5aS,6S,9R,9aR)- Cannabielsoic acid A (CBEA-C5 A) |
| 53. | (5aS,6S,9R,9aR)- Cannabielsoic acid B (CBEA-C5 B) |
| 54. | (5aS,6S,9R,9aR)- C3-Cannabielsoic acid B (CBEA-C3 B) |
| 55. | Cannabiglendol-C3 (OH-iso-HHCV-C3) |
| 56. | Dehydrocannabifuran (DCBF-C5) |
| 57. | Cannabifuran (CBF-C5) |
| 58. | (−)-Δ7-trans-(1R,3R,6R)-Isotetrahydrocannabinol |
| 59. | (±)-Δ7-1,2-cis- (1R,3R,6S/1S,3S,6R)- Isotetrahydro-cannabivarin |
| 60. | (−)-Δ7-trans-(1R,3R,6R)- Isotetrahydrocannabivarin |
| 61. | (±)-(1aS,3aR,8bR,8cR)- Cannabicyclol (CBL-C5) |
| 62. | (±)-(1aS,3aR,8bR,8cR)- Cannabicyclolic acid A (CBLA-C5 A) |
| 63. | (±)-(1aS,3aR,8bR,8cR)- Cannabicyclovarin (CBLV-C3) |
| 64. | Cannabicitran (CBT-C5) |
| 65. | Cannabichromanone (CBCN-C5) |
| 66. | Cannabichromanone-C3 (CBCN-C3) |
| 67. | Cannabicoumaronone (CBCON-C5) |
| 68. | Cannabielsoin acid A (CBEA-A) |
| 69. | 10-Ethoxy-9-hydroxy-delta-6a-tetrahydrocannabinol |
| 70. | Cannabitriolvarin (CBTV) |
| 71. | Delta-9-tetrahydrocannabiorcolic acid (THCA-C1) |
| 72. | Delta-7-cis-iso-tetrahydrocanna |
| 73. | Cannabichromanon (CBCF) |

Structure of common cannaboinoids

CBD

CBDA

CBDVA-OMe

THC

THCA

THCV

CBG

CBGA

CBGV

Structure of common cannaboinoids

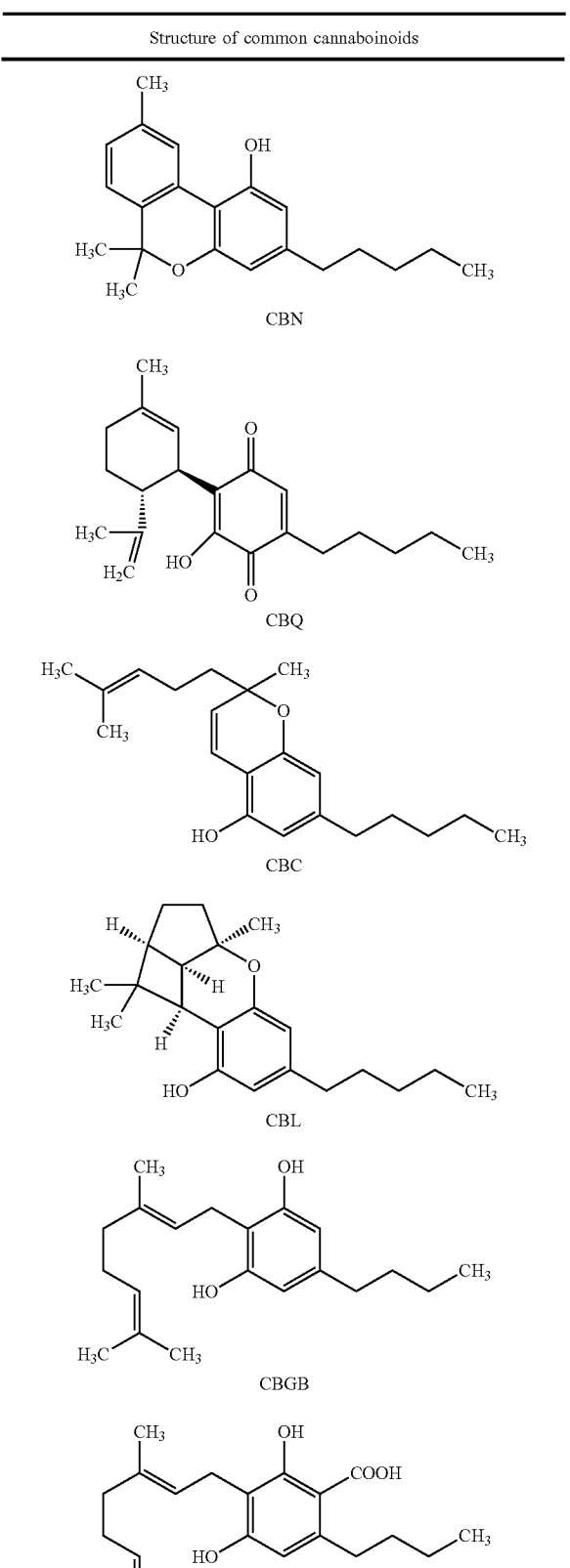

Structure of common cannaboinoids

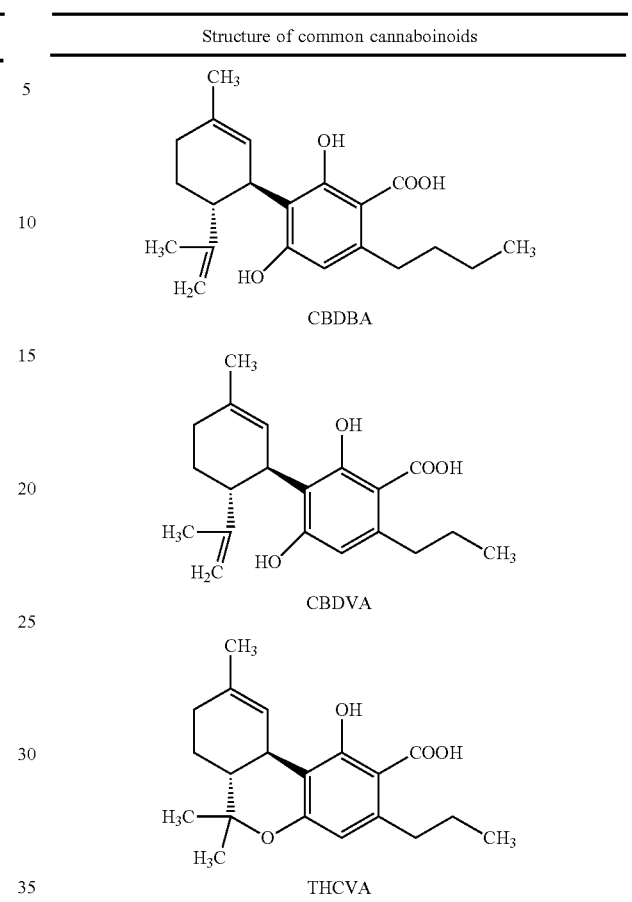

Synthetically prepared cannabinoids, that are commercially available (e.g., Purisys™ of Athens, GA), are provided below.

| Common Name | Other Names | Alkyl Tail Length | CAS # |
|---|---|---|---|
| TETRAHYDROCANNABIVARIN FAMILY | | | |
| Δ9-Tetrahydrocannabivarin | Δ9-THCV | C3 | 31262-37-0 |
| Δ8-Tetrahydrocannabivarin | Δ8-THCV | C3 | 31262-38-1 |
| Δ9-Tetrahydrocannabivarin Naphtoylester | Δ9-THCV-NE | C3 | N/A |
| Δ8-Tetrahydrocannabivarin Naphtoylester | Δ8-THCV-NE | C3 | N/A |
| Δ9-Tetrahydrocannabivarinic Acid | Δ9-THCVA-A, Δ9-THC-VA-B | C3 | 39986-26-0 |

| Common Name | Other Names | Alkyl Tail Length | CAS # |
|---|---|---|---|
| CANNABIDIOLVARIN FAMILY | | | |
| (−)-Cannabidivarin | (−)-CBDV | C3 | 24274-48-4 |
| (+)-Cannabidivarin | (+)-CBDV | C3 | 1637328-94-9 |
| Cannabidivarinic Acid | CBDVA | C3 | 31932-13-S |
| Cannabidivarin Quinone | CBQV | C3 | N/A |

| Common Name | Other Names | Alkyl Tail Length | CAS # |
|---|---|---|---|
| TETRAHYDROCANNABIBUTOL FAMILY | | | |
| Δ9-Tetrahydrocannabibutol | Δ9-THCB | C4 | 60008-00-6 |
| Δ8-Tetrahydrocannabibutol | Δ8-THCB | C4 | 51768-59-3 |
| Δ9-Tetrahydrocannabibutol Naphtoylester | Δ9-THCB-NE | C4 | 60007-98-9 |
| Δ8-Tetrahydrocannabibutol Naphtoylester | Δ8-THCB-NE | C4 | N/A |
| Δ9-Tetrahydrocannabibutolic Acid | Δ9-THCBA-A, Δ9-THC-BA-B | C4 | 60007-98-9 |

| Common Name | Other Names | Alkyl Tail Length | CAS # |
|---|---|---|---|
| CANNABIDIBUTOL FAMILY | | | |
| (−)-Cannabidibutol | (−)-CBDB | C4 | 60113-11-3 |
| (+)-Cannabidibutol | (+)-CBDB | C4 | N/A |
| Cannabidibutolic Acid | CBDBA | C4 | N/A |

| Common Name | Other Names | Alkyl Tail Length | CAS # |
|---|---|---|---|
| RARE CANNABINOIDS | | | |
| Cannabinol | CBN, USP Impurity | C5 | 521-35-7 |
| Cannabinolic Acid | CBNA | C5 | 2808-39-1 |
| Cannabigerol | CBG | C5 | 25654-31-3 |
| Cannabigerolic Acid | CBGA | C5 | 25555-57-1 |
| Cannabichromene | CBC | C5 | 20675-51-8 |
| Cannabichromenic Acid | CBCA | C5 | 185505-15-1 |
| Cannbicyclol | CBL | C5 | 21366-63-2 |
| Cannabicyclolic Acid | CBLA | C5 | 2283314-84-9 |
| Cannabivarin | CBNV | C3 | 33745-21-0 |
| Cannabivarinic Acid | CBNVA | C3 | 64846-02-2 |
| Cannbigerivarin | CBGV | C3 | 55824-11-8 |
| Cannabigerivarinic Acid | CBGVA | C3 | 64924-07-8 |
| Cannbichromevarin | CBCV | C3 | 57130-04-8 |
| Cannabichromevarinic Acid | CBCVA | C3 | 64898-02-8 |
| Cannabicyclolvarin | CBLV | C3 | 55870-47-8 |
| Cannabicyclolvarinic Acid | CBLVA | C3 | 2281847-63-8 |
| 3-Butylcannabinol | CBNB | C4 | 60007-99-0 |
| 3-Butylcannabinolic Acid | CBNBA | C4 | N/A |
| Cannabigerol Butyl | CBGB | C4 | N/A |
| Cannabigerol Butyric Acid | CBGBA | C4 | N/A |
| Cannabichromene Butyl | CBCB | C4 | N/A |
| Cannabichromene Buytric Acid | CBCBA | C4 | N/A |
| Cannabicyclol Butyl | CBLB | C4 | N/A |
| Cannabicyclol Butyric Acid | CBLBA | C4 | N/A |

The term "terpene" refers to a hydrocarbon or derivative thereof, found as a natural product and biosynthesized by oligomerization of isoprene units. A terpene can be acyclic, monocyclic, bicyclic, or multicyclic. Examples include, e.g., sesquiterpenes (e.g., (−)-β-caryophyllene, humulene, vetivazulene, guaiazulene, longifolene, copaene, and patchoulol), monoterpenes (e.g., limonene and pulegone), monoterpenoids (e.g., carvone), diterpenes (e.g., taxadiene), and triterpenes (e.g., squalene, betulin, betulinic acid, lupane, lupeol, betulin-3-caffeate, allobetulin, and cholesterol). The terpene can be synthetically prepared, or alternatively, can be obtained naturally (e.g., from plant matter). Either way, the terpene can have the requisite purity (e.g., at least 95 wt. % pure, at least 98 wt. % pure, at least 99 wt. % pure, or at least 99.5 wt. % pure).

| Terpene | Plant | Genus | Species |
|---|---|---|---|
| Myrcene | Myrtles | *Myrtus* | *communis*; *nivellei*; *phyllireaefolia* |
| | Cannabis | *Cannabis* | *sativa*; *ruderalis*; *indica* |

-continued

| Terpene | Plant | Genus | Species |
|---|---|---|---|
| Linalool | Mint | *Mentha* | *spicata; arvensis; canadensis* |
| | Lavender | *Lavandula* (subgenus: *Fabricia; Sabaudia*) | *spica; angustifolia; latifolia; lanata; dentata; stoechas; pedunculata; viridis* |
| Terpineol | Orange peel | *Citrus* | *reticulata* |
| | Junipers | *Juniperus* | *communis; chinensis; conferta; rigida* |
| Camphene | Chrysanthemum | *Chrysanthemum* | *indicum* |
| | Ginger | *Zingiber* | *officinale* |
| Bisabolol | Chamomile | *Matricaria* (or *Chamaemelum*) | *chamomilla* (or *nobile*) |
| | Figwort | *Myoporum* | *crassifolium* |
| Nerolidol | *Cannabis* | *Cannabis* | *sativa; ruderalis; indica* |
| Limonene | Citrus Lemon | *Citrus* | *limon* |
| Humulene | Hops | *Humulus* | *lupulus; japonicus; yunnanensis* |
| Terpinolene | *Cannabis* | *Cannabis* | *sativa; ruderalis; indica* |
| Carene | Rosemary | *Salvia* | *rosmarinus; jordanii* |
| | Cedar | *Cedrus* | *atlantica; brevifolia; deodara; libani* |
| Eucalyptol | Eucalyptus | *Eucalyptus* | *obliqua* |
| | Cannabis | *Cannabis* | *sativa; ruderalis; indica* |
| | Camphor laurel | *Cinnamomum* | *camphora* |
| | Bay leaves | *Laurus* | *nobilis* |
| | Wormwood | *Artemisia* | *vulgaris* |
| Ocimene | Hops | *Humulus* | *lupulus; japonicus; yunnanensis* |
| | Kumquats | *Citrus* | *japonica* |
| | Mango | *Mangifera* | *indica* |
| | Basil | *Ocimum* | *basilicum* |
| | bergamot orange | *Citrus* | *x aurantium* |
| Carophyllene | Peppercorn | *Piper* | *nigrum* |
| | Cloves | *Syzgium* | *aromaticum* |
| | Cannabis | *Cannabis* | *sativa; ruderalis; indica* |
| | Rosemary | *Salvia* | *rosmarinus; jordanii* |
| | Hops | *Humulus* | *lupulus; japonicus; yunnanensis* |
| Valencene | Nootka cypress | *Callitropsis* | *nootkatensis* |
| Geraniol | Roses | *Rosa* (subgenus: *Banksianae, Bracteatae, Caninae, Carolinae, Chinensis, Gallicanae, Gymnocarpae, Laevigatae, Pimpinellifoliae, Synstylae*) | *persica; minutifolia; stellata* |
| | Wine grapes | *Vitis* | *vinifera* |
| Borneol | Borneo camphor | *Dryobalanops* | *aromatica* |
| | Ngai camphor; sambong | *Blumea* | *balsamifera* |
| Pulegone | Catnip | *Nepeta* | *cataria* |
| | Peppermint | *Mentha* | *piperita* |
| | Pennyroyal | *Hedeoma* | *pulegioides* |
| Guaiazulene | Chamomile | *Matricaria* (or *Chamaemelum*) | *chamomilla* (or *nobile*) |
| | Guaiacum tree | *Guaiacum* | *sanctum, angustifolium, coulteri, officinale* |
| Lupeol | Lupine seed | *Lupinus* | *luteus* |
| Lupane | Lupine seed | *Lupinus* | *luteus* |
| Betulin Betulinic acid Lupeol | Brich tree | *Betula* (Subgenus: *Betulenta, Betulaster, Neurobetula, Chamaebetula*) | *alleghaniensis, cordifolia, glandulosa, lenta, michauxii, minor, nana, neoalaskana, nigra, occidentalis, papyrifera, populifolia, pumila, uber* |
| Squalene | Amaranth seed | *Amaranthus* (subgenus: *Acnida; Albersia*) | *acanthochiton, acutilobus, albus, anderssonii, californicus* |
| | Wheat germ | *Triticum* | *aestivum* |
| | Olive | *Olea* | *europaea* |
| Carvone | Caraway seed | *Carum* | *carvi* |
| | Spearmint | *Mentha* | *spicata* |
| | Dill | *Anethum* | *graveolens* |

-continued

| Terpene | Plant | Genus | Species |
|---|---|---|---|
| Patchoulol | Patchouli | *Pogostemon* | *cablin* |
| Copaene | Copaiba tree | *Copaifera* | *langsdorfii* |
| Longifolene | Pine | *Pinus* | *longifolia* |
| Pinene | Pine | *Pinus* (subgenus: *Strobus*; *Pinus*) | *densata, densiflora, pinea, sylvestris* |
| Vetivazulene | Vetiver | *Chrysopogon* | *zizanioides* |
| Nerol | Lemon Grass | *Cymbopogon* | *nardus; citratus; flexuosus; martinii; schoenanthus* |

Synthetically prepared terpenes, which are commercially available (e.g., Purisys™ of Athens, GA), are provided below.

| Terpene | CAS# |
|---|---|
| Alpha-Pinene | 51634232009 |
| Beta-Pinene | 51634232109 |
| Beta-Myrcene | 51634232209 |
| Alpha-Terpinene | 51634232309 |
| Limonene | 51634232409 |
| Beta-Ocimene | 51634232509 |
| Terpinolene | 51634232609 |
| Linalool | 51634232709 |
| Fenchyl Alcohol | 51634232809 |
| Borneol Isomers | 51634232909 |
| Alpha-Terpineol | 51634233009 |
| Trans-caryophyllene | 51634233109 |
| Alpha-humulene | 51634233209 |
| Trans-nerolidol | 51634233309 |

-continued

| Terpene | CAS# |
|---|---|
| Guaiol | 51634233409 |
| Alpha-Bisabolol | 51634233509 |

The term "flavonoid" refers to ubiquitous plant natural products with various polyphenolic structures. Flavonoids can be extracted from fruits, vegetables, grains, bark, roots, stems, flowers, and teas or can be biosynthetically produced. The role of flavonoids in plants includes UV protection, aid in plant growth, defense against plaques, and provide the color and aroma of flowers.

Flavonoids can be divided into classes (e.g., anthocyanin, chalcone, flavone, flavonol, isoflavone, and flavonone) and subclasses depending on the carbon of the C ring on which the B ring is attached and the degree of unsaturation and oxidation of the C ring.

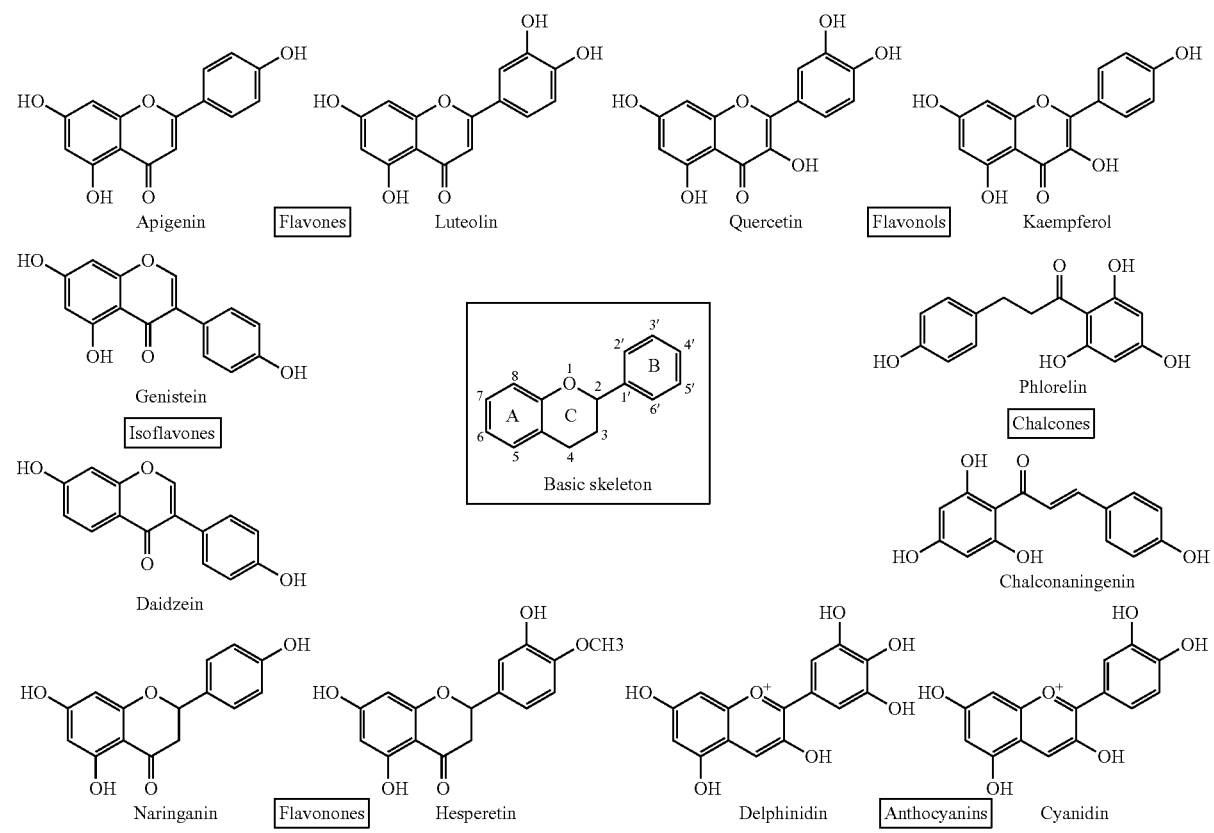

| Flavonoid classes | Structure of flavonoid classes |
|---|---|
| Anthocyanins | Double bonds between positions 1 and 2, 3 and 4 of the C ring; Hydroxyl groups at positions 5 and 7 in the A ring and 3', 4' and/or 5' of the B ring; Methylation or acylation at the hydroxyl groups on the A and B rings vary |
| Chaicones | Absence of 'C ring' of the basic flavonoid skeleton structure |
| Flavonones | C ring is saturated (contains no double bonds) |
| Flavones | Double bond between positions 2 and 3 and a ketone in position 4 of the C ring; Most have a hydroxyl group in position 5 or 7 of the A ring of the A ring or 3' and 4' of the B ring (varies according to the taxonomic classification of the particular plant) |
| Flavonols | Double bond between positions 2 and 3, a ketone in position 4 and hydroxyl group in position 3 of the C ring; the ketone group the C ring may also be glycosylated; very diverse in methylation and hydroxylation patterns |
| Isoflavonoids | B ring is attached to the 3 position of the C ring and contains a hydroxyl group at the 4' position; hydroxylation of the A ring varies |

| Flavonoid classes | Structure of flavonoid classes |
|---|---|
| Anthocyanins | Double bonds between positions 1 and 2, 3 and 4 of the C ring; Hydroxyl groups at positions 5 and 7 in the A ring and 3', 4' and/or 5' of the B ring; Methylation or acylation at the hydroxyl groups on the A and B rings vary |
| Chaicones | Absence of 'C ring' of the basic flavonoid skeleton structure |
| Flavonones | C ring is saturated (contains no double bonds) |
| Flavones | Double bond between positions 2 and 3 and a ketone in position 4 of the C ring; Most have a hydroxyl group in position 5 or 7 of the A ring of the A ring or 3' and 4' of the B ring (varies according to the taxonomic classification of the particular plant) |
| Flavonols | Double bond between positions 2 and 3, a ketone in position 4 and hydroxyl group in position 3 of the C ring; the ketone group the C ring may also be glycosylated; very diverse in methylation and hydroxylation patterns |
| Isoflavonoids | B ring is attached to the 3 position of the C ring and contains a hydroxyl group at the 4' position; hydroxylation of the A ring varies |

Studies on flavonoids have revealed an increasing number of health benefits showing anti-oxidant, anti-inflammatory, anti-mutagenic, and anti-carcinogenic properties by inhibiting numerous pro-inflammatory and pro-oxidative enzymes (e.g., xanthine oxidase (XO), cyclo-oxygenase (COS), lipoxygenase, phosphoinositide 3-kinase, and acetylcholinesterase). This may have benefits towards numerous diseases and medical conditions (e.g., pain, cancer, artherscle- rosis, Alzheimer's disease). There is a growing interest in the medicinal properties of Cannabis (Cannabis sativa, Cannabis indica, Cannabis ruderalis). Studies have shown that Cannaflavin A and Cannflavin B, prenylated flavones, have anti-inflammatory properties greater than aspirin. Cannflavin A and B can be isolated from Cannabis sativa and biosynthesized.

Synthetically prepared flavonoids, which are commercially available (e.g., Cannflavin B from Toronto Research Chemicals), are provided below.

| Flavonoid | CAS# |
|---|---|
| Cannflavin A | 76735-57-4 |
| Cannflavin B | 76735-58-5 |
| Myricetin | 529-44-2 |
| (−)-Epigallocatechin gallate | 989-51-5 |
| Polyphenon 60 from green tea | 138988-88-2 |
| (−)-Gallocatechin | 3371-27-5 |
| Kaempferol | 520-18-3 |
| (+)-Catechin hydrate | 7295-85-4 (anhydrous) |
| Galangin | 548-83-4 |
| Hesperidin | 520-26-3 |
| Baicalein | 491-67-8 |
| Icariin | 489-32-7 |
| Orientin | 28608-75-5 |
| Liquiritigenin | 578-86-9 |
| Acacetin | 480-44-4 |
| Diosmetin | 520-34-3 |
| Scutellarein | 529-53-3 |
| Luteolin | 491-70-3 |

The term "transdermal delivery agent" refers to a substance that aids or facilitates the passage of desired compounds, such as pharmaceutically active ingredients (e.g., external antibiotic agent), cannabinoids, and/or terpenes, at least partially through one or more layers of the skin, including the dermis and epidermis.

The term "skin surface" refers to interface of an organism with the environment, which prevents moisture loss from the body, and is a barrier functioning to prevent the invasion of biotoxic substances, such as microorganisms and allergens, from the environment. The skin contains two layers consisting of an outer epidermis and an inner dermis.

The term "human" refers to a person who can benefit from the pharmaceutical formulations and methods of the present invention. The person that could benefit from the presently described pharmaceutical formulations and methods may be an adolescent or adult. A human may be referred to as an individual, patient, subject, or recipient.

The term "topical formulation" is used herein to generally include a formulation that can be applied to skin or a mucosa. Topical formulations may, for example, be used to confer therapeutic benefit to a patient or cosmetic benefits to a consumer. Topical formulations can be used for both topical and transdermal administration of substances. The topical formulations can be configured and formulated to exist in various dosage forms, such as, e.g., gel, pump gel, gel packet, cream, lotion, roll-on liquid, roll-on gel, spray, pump spray, aerosol spray, stick, patch, ointment, liniment, or balm.

The term "topical administration" is used herein to generally include the delivery of a substance, such as a therapeutically active agent (e.g., external antibiotic agent), to the skin or a localized region of the body.

The term "transdermal administration" is used herein to generally include administration through at least a portion of the skin. Transdermal administration is often applied for delivering desired substances to tissues underlying the skin with minimal systemic absorption. As such, the transdermal administration delivers desired substances at least partially through one or more layers of the skin, including the dermis and epidermis.

The term "subject" is used herein to generally include humans, particularly humans at least 2 years of age, human adolescents (e.g., 12-17 years old) and human adults (e.g., at least 18 years old).

The term "effective amount" is used herein to generally include an amount of topical formulation (or external antibiotic agent) effective for treating or preventing infection in a subject as described herein.

The term "treating" with regard to a subject, refers to improving at least one symptom of the subject's disorder. Treating includes curing, improving, or at least partially ameliorating the disorder or the symptoms thereof.

Method of Manufacturing

As described herein, the compositions of the present invention are suitable for topical (e.g., dermal or intradermal) administration and include, e.g., liquid or semi-solid preparations (e.g., liniments, lotions, gels, sprays, foams, film forming systems, microneedles, micro- or nano-emulsions), and oil-in-water or water-in-oil emulsions (e.g., creams, ointments or pastes). These topical dosage forms can be prepared employing well-known and routine procedures, equipment, techniques, and substances. See, e.g., A. Williams, Transdermal and Topical Delivery Systems, Pharmaceutical Press, London and Chicago, 2003; L. Lachman, The Theory and Practice of Industrial Pharmacy, 4th Ed., Stipes Publishing, 2015; Remington, Pharmaceutical Sciences, $22^{nd}$ Rev., Pharmaceutical Press, 2012; H. Benson, Topical and Transdermal Drug Delivery: Principles and Practice 1st Edition, Wiley, 2012; D. Osborne, Topical Drug Delivery Formulations (Drugs and the Pharmaceutical Sciences) 1st Edition, CRC Press, 1989; and M. Brown, The Art and Science of Dermal Formulation Development (Drugs and the Pharmaceutical Sciences) 1st Edition, CRC Press, 2019.

EXAMPLES

Production Examples 1-50 below illustrate active ingredients (external antibiotic agents) formulated with suitable inactive ingredients to provide various dosage forms (e.g., ointments, creams, and lotions). As described herein, the formulations illustrated in Production Examples 1-50 can be formulated to further include a cannabinoid, terpene, flavonoid, or combination thereof.

Production Example 1

Topical First Aid Antibiotic: bacitracin zinc ointment
ACTIVE INGREDIENT: Bacitracin Zinc 500 units
INACTIVE INGREDIENTS: white petrolatum Production Example 2

Topical First Aid Antibiotic: bacitracin zinc ointment
ACTIVE INGREDIENT: BACITRACIN ZINC 500 [iU] in 1 g
INACTIVE INGREDIENTS: PETROLATUM, LIGHT MINERAL OIL, MINERAL OIL Production Example 3

Topical First Aid Antibiotic: bacitracin zinc ointment
ACTIVE INGREDIENT (IN EACH GRAM): Bacitracin Zinc (equal to 500 bacitracin units)
INACTIVE INGREDIENTS: hard paraffin, liquid paraffin, white soft paraffin, lanolin Production Example 4

Topical First Aid Antibiotic: bacitracin zinc ointment
ACTIVE INGREDIENT (EACH GRAM CONTAINS): Bacitracin zinc 500 units
INACTIVE INGREDIENT: mineral oil, white petrolatum Production Example 5

Topical First Aid Antibiotic: bacitracin zinc ointment
ACTIVE INGREDIENT: Bacitracin Zinc 500 Units per gram
INACTIVE INGREDIENTS: Aloe vera gel, light mineral oil, white petrolatum Production Example 6

Topical First Aid Antibiotic: bacitracin zinc ointment
ACTIVE INGREDIENT (IN EACH GRAM): Bacitracin zinc (500 units bacitracin)
INACTIVE INGREDIENTS: mineral oil, petrolatum Production Example 7

Topical First Aid Antibiotic: bacitracin ointment
ACTIVE INGREDIENT: Bacitracin 500 units
INACTIVE INGREDIENT: light mineral oil, white petrolatum Production Example 8

Topical First Aid Antibiotic: bacitracin ointment
ACTIVE INGREDIENT: Bacitracin (500 units in each gram)
INACTIVE INGREDIENTS: Hard Paraffin, Liquid Paraffin, White Soft Paraffin Production Example 9

Topical First Aid Antibiotic: bacitracin zinc ointment
ACTIVE INGREDIENT: Bacitracin zinc 500 units
INACTIVE INGREDIENT: petrolatum Production Example 10

Topical First Aid Antibiotic: bacitracin zinc ointment
ACTIVE INGREDIENT: Bacitracin Zinc (500 units in each gram)
INACTIVE INGREDIENTS: Hard Paraffin, Liquid Paraffin, White Soft Paraffin Production Example 11

Topical First Aid Antibiotic with Pain Relief: bacitracin and lidocaine ointment
ACTIVE INGREDIENTS: Bacitracin, USP 500 units (First Aid Antibiotic) and Lidocaine 4% w/w (Pain Reliever)
INACTIVE INGREDIENT: white petrolatum

Production Example 12

Topical First Aid Antibiotic: bacitracin zinc ointment
ACTIVE INGREDIENT (IN EACH GRAM): Bacitracin Zinc (equal to 500 Bacitracin Units)
INACTIVE INGREDIENTS: Hard Paraffin, Liquid Paraffin, White Soft Paraffin and Lanolin Production Example 13

Topical First Aid Antibiotic: neomycin sulfate ointment
ACTIVE INGREDIENT (IN EACH GRAM): Neomycin sulfate 5 mg (neomycin 3.5 mg) (First aid antibiotic)
INACTIVE INGREDIENTS: lanolin, methylparaben, petrolatum, propylparaben, vitamin A palmitate

Production Example 14

Topical First Aid Antibiotic: neomycin sulfate ointment
ACTIVE INGREDIENT (EACH GRAM CONTAINS): Neomycin sulfate (equivalent to 3.5 mg Neomycin base)
INACTIVE INGREDIENT: Petrolatum Production Example 15

Topical First Aid Antibiotic: neomycin sulfate ointment
ACTIVE INGREDIENT (IN EACH GRAM): Neomycin Sulfate 3.5 mg
INACTIVE INGREDIENTS: Liquid paraffin, Cethanol, Squalane, Purified lanolin, White petrolatum, Cetearyl alcohol, Tocopheryl acetate, Methylparaben, Propylparaben

Production Example 16

Topical First Aid Antibiotic: neomycin sulfate ointment
ACTIVE INGREDIENT (IN EACH GRAM): Neomycin 3.5 mg
INACTIVE INGREDIENTS: Cetyl alcohol, Light Mineral Oil, Methylparaben, Propylparaben, Squalane, Tocopheryl acetate, White petrolatum

Production Example 17

Topical First Aid Antibiotic: neomycin sulfate ointment
ACTIVE INGREDIENT (in each gram): Neomycin sulfate 3.5 mg
INACTIVE INGREDIENT: cetanol, ethanol, liquid paraffin, methylparaben, petrolatum, propylparaben, purified lanolin, squalane, tocopherol acetate

Production Example 18

Topical First Aid Antibiotic: neomycin sulfate ointment
ACTIVE INGREDIENT (in each gram): Neomycin sulfate equivalent to 3.5 mg
INACTIVE INGREDIENT: methylparaben, propylparaben, vitamin E, white petrolatum

Production Example 19

Topical First Aid Antibiotic: neomycin sulfate ointment
ACTIVE INGREDIENT (IN EACH GRAM): Neomycin Sulfate (3.5 mg Neomycin)
INACTIVE INGREDIENTS: mineral oil, petrolatum

Production Example 20

Topical First Aid Antibiotic: tetracycline hydrochloride ointment
ACTIVE INGREDIENT: Tetracycline (3%)
INACTIVE INGREDIENTS: Water, glycerin, hydroxethylcellulose, chlorhexidine gluconate, glucono delta lactone, methylparaben, sodium hydroxide, dipropylene glycol, dimethyl sulfoxide, sorbic acid, ascorbic acid, magnesium stearate, stearic acid, sodium bicarbonate.

Production Example 21

Topical First Aid Antibiotic: tetracycline hydrochloride ointment
ACTIVE INGREDIENT (IN EACH GRAM): Tetracycline Hydrochloride 30 mg
INACTIVE INGREDIENT: Acetic Acid, Ascorbic Acid, chlorhexidine gluconate, cholecalciferol, dimethyl sulfoxide, dipropylene glycol, glucono delta lactone, GLYCERIN, histidine, hydroxethylc-cellulose, magnesium stearate, methylparaben, sodium hydroxide, sorbic acid, steric acid, water.

Production Example 22

Topical First Aid Antibiotic: tetracycline hydrochloride ointment
ACTIVE INGREDIENT (IN EACH GRAM): Tetracycline hydrochloride 30 mg
INACTIVE INGREDIENTS: ASCORBIC ACID, CHLORHEXIDINE GLUCONATE, CHOLECALCIFEROL, DIMETHYL SULFOXIDE, DIPROPYLENE GLYCOL, GLUCONO DELTA LACTONE, GLYCERIN, HYDROXETHYLCELLULOSE, MAGNESIUM STEARATE, METHYLPARABEN, SODIUM HYDROXIDE, SORBIC ACID, STEARIC ACID, WATER

Production Example 23

Topical First Aid Antibiotic: tetracycline hydrochloride ointment
ACTIVE INGREDIENT: Tetracycline hydrochloride 3%
INACTIVE INGREDIENTS: ascorbic acid (vitamin C), cholecalciferol (vitamin D3), dimethyl sulfoxide, dipropylene glycol

Production Example 24

Topical First Aid Antibiotic: tetracycline hydrochloride ointment
ACTIVE INGREDIENT: Tetracycline (3%)
INACTIVE INGREDIENTS: Water, glycerin, hydroxethylcellulose, chlorhexidine gluconate, glucono delta lactone, methylparaben, sodium hydroxide, dipropylene glycol, dimethyl sulfoxide, sorbic acid, ascorbic acid, magnesium stearate, stearic acid.

Production Example 25

Topical First Aid Antibiotic: tetracycline hydrochloride ointment
ACTIVE INGREDIENT: Tetracycline (3%)
INACTIVE INGREDIENTS: Water, glycerin, hydroxethylcellulose, chlorhexidine gluconate, glucono delta lactone, methylparaben, sodium hydroxide, dipropylene glycol, dimethyl sulfoxide, sorbic acid, ascorbic acid, magnesium stearate, stearic acid.

Production Example 26

Topical First Aid Antibiotic: tetracycline hydrochloride ointment
ACTIVE INGREDIENT (IN EACH GRAM): Tetracycline Hydrochloride 30 mg
INACTIVE INGREDIENTS: Ascorbic Acid, Cholecalciferol, Diazolidinyl Urea*, Dimethyl Sulfoxide, Dipropylene Glycol, Glucono Delta Lactone*, Glycerin, Polysorbate 80*, Propylene Glycol*, Sodium Hydroxide, Water (*Contains one or more of these ingredients)

Production Example 27

Topical First Aid Antibiotic: tetracycline hydrochloride ointment
ACTIVE INGREDIENT: Tetracycline hydrochloride 3%
INACTIVE INGREDIENTS: Water, glycerin, hydroxethylcellulose, chlor-hexide gluconate, glucono delta lactone, methylparaben, sodium hydroxide, dipropylene glycol, dimethyl sulfoxide, sorbic acid, ascorbic acid, magnesium stearate, stearic acid

Production Example 28

Topical First Aid Antibiotic: tetracycline hydrochloride ointment
ACTIVE INGREDIENT (IN EACH GRAM): Tetracycline hydrochloride 30 mg
INACTIVE INGREDIENTS: Acetic Acid, Ascorbic Acid, Chlorhexidine Gluconate, Cholecalciferol, Dimethyl Sulfoxide, Dipropylene Glycol, Glucono Delta Lactone, Glycerin, Histidine, Hydroxethyl-cellulose, Magnesium Stearate, Methylparaben, Sodium Hydroxide, Sorbic Acid, Stearic Acid, Water

Production Example 29

Topical First Aid Antibiotic: bacitracin zinc and polymyxin b sulfate ointment
ACTIVE INGREDIENTS (IN EACH GRAM): Bacitracin Zinc (equal to 500 bacitracin units);
Polymyxin B Sulfate (equal to 10,000 polymyxin B units)
INACTIVE INGREDIENTS: petrolatum

Production Example 30

Topical First Aid Antibiotic: bacitracin zinc and polymyxin b sulfate ointment
ACTIVE INGREDIENT: Bacitracin zinc 500 units; Polymyxin B sulfate 10,000 units
INACTIVE INGREDIENT: white petrolatum

Production Example 31

Topical First Aid Antibiotic: bacitracin zinc, neomycin sulfate and polymyxin b sulfate ointment
ACTIVE INGREDIENTS: Bacitracin Zinc 400 Units; Neomyxin Sulfate 5 mg (Equivalent to 3.5 mg Neomyxin); Polymyxin B Sulfate 5000 Units
INACTIVE INGREDIENT: White petrolatum

Production Example 32

Topical First Aid Antibiotic: bacitracin zinc, neomycin sulfate and polymyxin b sulfate ointment
ACTIVE INGREDIENTS: Bacitracin Zinc 400 Units; Neomyxin Sulfate 5 mg (Equivalent to 3.5 mg Neomyxin); Polymyxin B Sulfate 5000 Units
INACTIVE INGREDIENTS: Hard Paraffin, Liquid Paraffin, White Soft Paraffin

Production Example 33

Topical First Aid Antibiotic and Pain Relief: neomycin sulfate, polymyxin b sulfate, pramoxine hydrochloride cream
ACTIVE INGREDIENTS (IN EACH GRAM): Neomycin 3.5 mg; Polymyxin B sulfate, USP 10,000 units; Pramoxine hydrochloride, USP 10 mg
INACTIVE INGREDIENTS: emulsifying wax, methylparaben, mineral oil, poloxamer 188, propylene glycol, purified water, white petrolatum

Production Example 34

Topical First Aid Antibiotic: bacitracin zinc, neomycin sulfate and polymyxin b sulfate ointment
ACTIVE INGREDIENTS (IN EACH GRAM): Bacitracin zinc (bacitracin 400 units); Neomycin sulfate (neomycin 3.5 mg); Polymyxin B sulfate (polymyxin B 5,000 units).
INACTIVE INGREDIENTS: Mineral oil, petrolatum, purified water

Production Example 35

Topical First Aid Antibiotic and Pain Relief: neomycin sulfate, polymyxin b sulfate and pramoxine hydrochloride cream
ACTIVE INGREDIENTS: Neomycin sulfate 3.5 mg; Polymyxin B sulfate 10,000 units;
Pramoxine HCl 10 mg
INACTIVE INGREDIENTS: cetyl alcohol, methylparaben, mineral oil, petrolatum, polysorbate 60, propylene glycol, propylparaben, purified water, sorbitan monostearate, stearic acid

Production Example 36

Topical First Aid Antibiotic and Pain Relief: neomycin sulfate, polymyxin b sulfate, and pramoxine hydrochloride cream
ACTIVE INGREDIENTS: Neomycin sulfate 3.5 mg; Polymyxin B sulfate 10,000 units;
Pramoxine HCl 10 mg
INACTIVE INGREDIENTS: emulsifying wax, methylparaben, mineral oil, propylene glycol, purified water, white petrolatum

Production Example 37

Topical First Aid Antibiotic and Pain Relief: bacitracin zinc, neomycin sulfate, polymyxin b sulfate, lidocaine ointment
ACTIVE INGREDIENTS (in each gram): Bacitracin zinc (400 units Bacitracin); Neomycin sulfate (3.5 mg neomycin); Polymyxin B sulfate (5000 units); Lidocaine 0.40 mg
INACTIVE INGREDIENT: white petrolatum

Production Example 38

Topical First Aid Antibiotic and Pain Relief: neomycin sulfate; polymyxin b sulfate; pramoxine hydrochloride cream
ACTIVE INGREDIENTS: Neomycin Sulfate 3.5 mg; Polymyxin B Sulfate 10,000 units;
Pramoxine HCl 10 mg
INACTIVE INGREDIENT: cetyl alcohol, methylparaben, mineral oil, petrolatum, polysorbate 60, propylene glycol, propylparaben, purified water, sorbitan monostearate, stearic acid

Production Example 39

Topical First Aid Antibiotic and Pain Relief: neomycin sulfate, polymyxin b sulfate, and pramoxine hydrochloride cream
ACTIVE INGREDIENTS: Neomycin sulfate 3.5 mg; Polymyxin B sulfate 10,000 units; Pramoxine hydrochloride 10 mg
INACTIVE INGREDIENTS: emulsifying wax, methylparaben, mineral oil, propylene glycol, purified water, white petrolatum

Production Example 40

Topical First Aid Antibiotic: bacitracin zinc, neomycin sulfate and polymyxin b sulfate ointment
ACTIVE INGREDIENTS: Bacitracin zinc 400 units; Neomycin sulfate 3.5 mg; Polymyxin B sulfate 5,000 units
INACTIVE INGREDIENT: white petrolatum

Production Example 41

Topical First Aid Antibiotic and Pain Relief: bacitracin zinc, polymyxin b sulfate, neomycin sulfate, and pramoxine hydrochloride ointment
ACTIVE INGREDIENT: Bacitracin 500 units; Neomycin 3.5 mg; Polymyxin B 10,000 units; Pramoxine hydrochloride 10 mg
INACTIVE INGREDIENT: Petrolatum

Production Example 42

Topical First Aid Antibiotic: bacitracin zinc, neomycin sulfate and polymyxin b sulfate ointment
ACTIVE INGREDIENTS (in each gram): Bacitracin Zinc 400 units; Neomycin Sulfate 5 mg (3.5 mg of Neomycin base); Polymyxin-B Sulfate 5000 units
INACTIVE INGREDIENTS: cocoa butter, cottonseed oil, olive oil, sodium pyruvate, vitamin E, white petrolatum

Production Example 43

Topical First Aid Antibiotic: bacitracin zinc, neomycin sulfate and polymyxin b sulfate ointment
ACTIVE INGREDIENTS (in each gram): Bacitracin 400 units; Neomycin 3.5 mg; Polymyxin B sulfate 5,000
INACTIVE INGREDIENTS: *Gossypium Herbaceum* (cotton) seed oil, *Olea Europaea* (olive) Fruit oil, *Theobroma Cacao* (cocoa) seed butter, sodium pyruvate, Tocopheryl Acetate, White Petrolatum

Production Example 44

Topical First Aid Antibiotic: bacitracin zinc, neomycin sulfate and polymyxin b sulfate ointment
ACTIVE INGREDIENTS (in each gram): Bacitracin 400 units; Neomycin 3.5 mg; Polymyxin B 5,000 units
INACTIVE INGREDIENTS: cocoa butter, cottonseed oil, olive oil, sodium pyruvate, vitamin E, white petrolatum

Production Example 45

Topical First Aid Antibiotic and Burn Relief: bacitracin zinc, neomycin sulfate, polymyxin b sulfate, and pramoxine hydrochloride ointment
ACTIVE INGREDIENT (in each gram): Bacitracin Zinc (500 units); Neomycin Sulfate (3.5 mg); Polymyxin B Sulfate (10,000 units); Pramoxine HCl (10 mg)
INACTIVE INGREDIENT: petrolatum

Production Example 46

Topical First Aid Antibiotic and Pain Relief: bacitracin zinc, neomycin sulfate, polymyxin b sulfate, and pramoxine hydrochloride ointment
ACTIVE INGREDIENTS (in each gram): Bacitracin Zinc (500 units); Neomycin Sulfate (3.5 mg); Polymyxin B Sulfate (10,000 units); Pramoxine HCl (10 mg)
INACTIVE INGREDIENT: Petrolatum

Production Example 47

Topical First Aid Antibiotic and Pain Relief: neomycin, polymyxin b, and pramoxine hydrochloride cream
ACTIVE INGREDIENTS (in each gram): Neomycin 3.5 mg; Polymyxin B 10,000 units; Pramoxine HCl 10 mg
INACTIVE INGREDIENTS: emulsifying wax, methylparaben, mineral oil, propylene glycol, purified water, white petrolatum

Production Example 48

Topical First Aid Antibiotic and Pain Relief: neomycin sulfate, polymyxin b sulfate, and pramoxine hydrochloride cream
ACTIVE INGREDIENTS (in each gram): Neomycin Sulfate (3.5 mg); Polymyxin B Sulfate (10,000 units); Pramoxine HCl (10 mg)
INACTIVE INGREDIENTS: Water, Emulsifying Wax, Mineral Oil, Petrolatum, Propylene Glycol, Methylparaben, Sulfuric acid, Sodium Hydroxide

Production Example 49

Topical First Aid Antibiotic and Pain Relief: bacitracin zinc, neomycin sulfate, polymyxin b sulfate, and pramoxine hydrochloride ointment
ACTIVE INGREDIENTS (in each gram): Bacitracin 500 units; Neomycin 3.5 mg; Polymyxin B 10,000 units; Pramoxine HCl 10 mg
INACTIVE INGREDIENT: white petrolatum Production Example 50

Topical First Aid Antibiotic Ointment

ACTIVE INGREDIENT: at least one of bacitracin, bacitracin zinc, neomycin, neomycin sulfate, tetracycline, tetracycline hydrochloride, and polymyxin b sulfate.

INACTIVE INGREDIENT: at least one of petrolatum, white petrolatum, hard paraffin, liquid paraffin, and white soft paraffin Production Example 51

Active ingredients (external antibiotics)

Active ingredients (external antibiotics) suitable for formulation with: (1) suitable inactive ingredients (excipients), and (2) a cannabinoid, terpene, flavonoid, or combination thereof, to provide various topical dosage forms (e.g., creams, gels, lotions, etc.).

TABLE 1

| ACTIVE | AMOUNT |
| --- | --- |
| Bacitracin Zinc | 500 units |
| Bacitracin Zinc | 500 units per gram |
| Bacitracin/Lidocaine | 500 units/4 wt. % |
| Neomycin sulfate | 3.5 mg |
| Tetracycline | 3 wt. % |
| Tetracycline hydrochloride | 30 mg per gram |
| Tetracycline hydrochloride | 3 wt. % |
| Bacitracin zinc and Polymyxin B sulfate | 500 units/10,000 units |
| Bacitracin zinc, neomycin sulfate, Polymyxin b sulfate | 400 units/3.5 mg/5000 units |
| Neomycin sulfate, Polymyxin b sulfate, Pramoxine hydrochloride | 3.5 mg/10,000 units/10 mg |
| Bacitracin zinc, Neomycin sulfate, Polymyxin b sulfate, Lidocaine | 400 units/3.5 mg/5000 units/0.40 mg |
| Bacitracin zinc, Neomycin sulfate, Polymyxin b sulfate, Pramoxine hydrochloride | 500 units/3.5 mg/10,000 units/10 mg |

TABLE 2

| ACTIVE | DOSAGE FORM & STRENGTHS |
| --- | --- |
| gentamicin sulfate | Cream: 0.1 wt. % Ointment: 0.1 wt. % |

TABLE 3

| ACTIVE | AMOUNT | Monograph | Subcategory |
| --- | --- | --- | --- |
| bacitracin | 500 units/g | first aid antibiotic | ointment |
| bacitracin zinc | 400 units/g | first aid antibiotic | ointment |
| chlortetracycline hydrochloride | 1 wt. % | first aid antibiotic | ointment |
| neomycin sulfate | EQ 3.5 mg base/g (mixed with neomycin sulfate and bacitracin zinc); EQ 1.75 mg base/mL (solution) | first aid antibiotic | ointment |
| oxytetracycline hydrochloride (combination only) | EQ 5 mg base/g | first aid antibiotic | ointment |
| polymyxin b sulfate (combination only) | 10,000 units/g (mixed with bacitracin zinc and neomycin sulfate); 10,000 units/g (mixed with Oxytetracycline hydrochloride); 10,000 units/mL (solution with gramicidin/neomycin sulfate); 5,000 units/g mixed with bacitracin and neomycin | first aid antibiotic | ointment |
| tetracycline hydrochloride | 10 mg/g | first aid antibiotic | ointment |
| neomycin ointment (combination only) | EQ 3.5 mg base/gm (mixed with bacitracin zinc and polymyxin b sulfate) | first aid antibiotic | ointment |
| neomycin sulfate cream | 5 mg/0.9 g | first aid antibiotic | cream |

ENUMERATED EMBODIMENTS

Specific enumerated embodiments <1> to <118> provided below are for illustration purposes only, and do not otherwise limit the scope of the disclosed subject matter, as defined by the claims. These enumerated embodiments encompass all combinations, sub-combinations, and multiply referenced (e.g., multiply dependent) combinations described therein.

<1> A topical antibiotic including the formulation of any one of Production Examples 1-51, further including a cannabinoid, terpene, flavonoid, or combination thereof.

<2> A topical antibiotic including the formulation of any one of Production Examples 1-51, further including a cannabinoid.

<3> A topical antibiotic including the formulation of any one of Production Examples 1-51, further including a cannabinoid obtained as a distillate from *cannabis*.

<4> A topical antibiotic including the formulation of any one of Production Examples 1-51, further including a cannabinoid obtained as an extract from *cannabis*.

<5> A topical antibiotic including the formulation of any one of Production Examples 1-51, further including a cannabinoid obtained as a resin from *cannabis*.

<6> A topical antibiotic including the formulation of any one of Production Examples 1-51, further including a cannabinoid isolate obtained from *cannabis*.

<7> A topical antibiotic including the formulation of any one of Production Examples 1-51, further including a cannabinoid obtained from *Cannabis* indica, *Cannabis ruderalis*, or *Cannabis sativa*.

<8> A topical antibiotic including the formulation of any one of Production Examples 1-51, further including a cannabinoid present as an oil from *cannabis*.

<9> A topical antibiotic including the formulation of any one of Production Examples 1-51, further including a cannabinoid present as hempseed oil.

<10> A topical antibiotic including the formulation of any one of Production Examples 1-51, further including a cannabinoid that is synthetically prepared.

<11> A topical antibiotic including the formulation of any one of Production Examples 1-51, further including a cannabinoid that is at least one of THC (tetrahydrocannabinol), THCA (tetrahydrocannabinolic acid), CBD (cannabidiol), CBDA (cannabidiolic acid), CBN (cannabinol), CBG (cannabigerol), CBC (cannabichromene), CBL (cannabicyclol) CBV (cannabivarin), THCV (tetrahydrocannabivarin), CBDV (cannabidivarin), CBCV (cannabichromevarin), CBGV (cannabigerovarin), CBGM (cannabigerol monomethyl ether), CBE (cannabielsoin), and CBT (cannabicitran).

<12> A topical antibiotic including the formulation of any one of Production Examples 1-51, further including a cannabinoid that is at least one of CBD and THC.

<13> A topical antibiotic including the formulation of any one of Production Examples 1-51, further including a terpene.

<14> A topical antibiotic including the formulation of any one of Production Examples 1-51, further including a terpene that is a sesquiterpene.

<15> A topical antibiotic including the formulation of any one of Production Examples 1-51, further including a terpene obtained as a distillate from plant matter.

<16> A topical antibiotic including the formulation of any one of Production Examples 1-51, further including a terpene obtained as an extract from plant matter.

<17> A topical antibiotic including the formulation of any one of Production Examples 1-51, further including a terpene obtained as a resin from plant matter.

<18> A topical antibiotic including the formulation of any one of Production Examples 1-51, further including a terpene obtained from *Cannabis sativa, Syzygium aromaticum* (cloves), rosemary, or hops.

<19> A topical antibiotic including the formulation of any one of Production Examples 1-51, further including a terpene that is synthetically prepared.

<20> A topical antibiotic including the formulation of any one of Production Examples 1-51, further including a terpene that is Beta-Caryophyllene <21> The topical antibiotic of any one of the above embodiments, wherein the amount of active ingredient expressed in terms of concentration (weight percent), present in the formulation of the any one of Production Examples 1-51, remains unchanged with the addition of the cannabinoid, terpene, flavonoid, or combination thereof. For Example, if the amount of active ingredient present in the formulation of the any one of Production Examples 1-51 is 3 wt. % tetracycline hydrochloride. With the addition of the cannabinoid, terpene, flavonoid, or combination thereof, the resulting amount of the tetracycline hydrochloride will remain at 3 wt. %.

<22> The topical antibiotic of any one of the above embodiments, wherein the amount of inactive ingredient expressed in terms of concentration (weight percent), present in the formulation of the any one of Production Examples 1-51, decreases with the amount added of the cannabinoid, terpene, flavonoid, or combination thereof. For Example, if the amount of active ingredient present in the formulation of the any one of Production Examples 1-51 is 3 wt. % tetracycline hydrochloride, with the addition of the cannabinoid, terpene, flavonoid, or combination thereof, the resulting amount of the tetracycline hydrochloride will be less than 3 wt. %.

<23> The topical antibiotic of any one of the above embodiments, wherein the aggregate amount of inactive ingredients, present in the formulation of the any one of Production Examples 1-51, decreases in proportion to the amount added of the cannabinoid, terpene, flavonoid, or combination thereof. For Example, if the aggregate amount of inactive ingredients present in the formulation of the any one of Production Examples 1-51 is 90 wt. %. With the addition of 1 wt. % of cannabinoid, terpene, flavonoid, or combination thereof, the resulting aggregate amount of those inactive ingredients will be 89 wt. %.

<24> The topical antibiotic of any one of the above embodiments, wherein the aggregate amount of active ingredient and inactive ingredient in terms of concentration (weight percent), present in the formulation of the any one of Production Examples 1-51, decreases in proportion to the amount added of the cannabinoid, terpene, flavonoid, or combination thereof. For Example, the aggregate amount of active and inactive ingredients present in the formulation of the any one of Production Examples 1-51 is 100 wt. %. With the addition of 1 wt. % of cannabinoid, terpene, flavonoid, or combination thereof, the resulting aggregate amount of those active and inactive ingredients will be 99 wt. %.

<25> The topical antibiotic of any one of the above embodiments, wherein the cannabinoid, terpene, flavonoid, or combination thereof, is present in an aggregate amount of up to 20 wt. %.

<26> The topical antibiotic of any one of the above embodiments, wherein the cannabinoid, terpene, flavonoid, or combination thereof, is present in an aggregate amount of up to 10 wt. %.

<27> The topical antibiotic of any one of the above embodiments, wherein the cannabinoid, terpene, flavonoid, or combination thereof, is present in an aggregate amount of up to 5 wt. %.

<28> The topical antibiotic of any one of the above embodiments, wherein the cannabinoid, terpene, flavonoid, or combination thereof, is present in an aggregate amount of up to 1 wt. %.

<29> The topical antibiotic of any one of the above embodiments, wherein the cannabinoid, terpene, flavonoid, or combination thereof, is present in an aggregate amount of up to 0.5 wt. %.

<30> The topical antibiotic of any one of the above embodiments, wherein the cannabinoid, terpene, flavonoid, or combination thereof, is present in an aggregate amount of 0.330±0.1 wt. %.

<31> The topical antibiotic of any one of the above embodiments, wherein the cannabinoid, terpene, flavonoid, or combination thereof, is present in an aggregate amount of 0.1 to 20 wt. %.

<32> The topical antibiotic of any one of the above embodiments, wherein the cannabinoid, terpene, flavonoid, or combination thereof, is present in an aggregate amount of 0.1 to 10 wt. %.

<33> The topical antibiotic of any one of the above embodiments, wherein the cannabinoid, terpene, flavonoid, or combination thereof, is present in an aggregate amount of 0.1 to 5 wt. %.

<34> The topical antibiotic of any one of the above embodiments, wherein the cannabinoid, terpene, flavonoid, or combination thereof, is present in an aggregate amount of 0.01 to 2.5 wt. %.

<35> The topical antibiotic of any one of the above embodiments, wherein the cannabinoid, terpene, flavonoid, or combination thereof, is present in an aggregate amount of 0.01 to 1 wt. %.

<36> The topical antibiotic of any one of the above embodiments, wherein the cannabinoid, terpene, flavonoid, or combination thereof, is present in an aggregate amount of 0.01 to 0.5 wt. %.

<37> The topical antibiotic of any one of the above embodiments, wherein the cannabinoid, terpene, flavonoid, or combination thereof, is present in an aggregate amount of 1 to 20 wt. %.

<38> The topical antibiotic of any one of the above embodiments, wherein the cannabinoid, terpene, flavonoid, or combination thereof, is present in an aggregate amount of 1 to 10 wt. %.

<39> The topical antibiotic of any one of the above embodiments, wherein the cannabinoid, terpene, flavonoid, or combination thereof, is present in an aggregate amount of 1 to 5 wt. %.

<40> The topical antibiotic of any one of the above embodiments, wherein the cannabinoid, terpene, flavonoid, or combination thereof, is present in an aggregate amount of 0.05 to 2.5 wt. %.

<41> The topical antibiotic of any one of the above embodiments, wherein the cannabinoid, terpene, flavonoid, or combination thereof, is present in an aggregate amount of 0.05 to 1 wt. %.

<42> The topical antibiotic of any one of the above embodiments, wherein the cannabinoid, terpene, flavonoid, or combination thereof, is present in an aggregate amount of 0.05 to 0.5 wt. %.

<43> The topical antibiotic of any one of the above embodiments, which is in the form of a gel, pump gel, gel packet, cream, lotion, roll-on liquid, roll-on gel, spray, pump spray, aerosol spray, stick, patch, ointment, liniment, or balm.

<44> A topical antibiotic including the formulation of any one of Production Examples 1-51, further including a cannabinoid, terpene, flavonoid, or combination thereof; wherein the cannabinoid, terpene, flavonoid, or combination thereof, while present in the aggregate amounts, are characterized as inactive ingredients.

<45> A topical antibiotic including the formulation of any one of Production Examples 1-51, further including a cannabinoid, terpene, flavonoid, or combination thereof; wherein the cannabinoid, terpene, flavonoid, or combination thereof, while present in the aggregate amounts, are characterized as an excipient.

<46> A topical antibiotic including the formulation of any one of Production Examples 1-51, further including a cannabinoid, terpene, flavonoid, or combination thereof; wherein the cannabinoid, terpene, flavonoid, or combination thereof, while present in the aggregate amounts, are characterized as active ingredients.

<47> A topical antibiotic including the formulation of any one of Production Examples 1-51, further including a cannabinoid, terpene, flavonoid, or combination thereof; wherein the cannabinoid, terpene, flavonoid, or combination thereof, while present in the aggregate amounts, are characterized as an antibiotic.

<48> A topical antibiotic including the formulation of Production Example 50, further including a cannabinoid, terpene, flavonoid, or combination thereof, and a carrier system.

<49> A topical antibiotic including the formulation of Production Example 50, further including a cannabinoid, and a carrier system.

<50> A topical antibiotic including the formulation of Production Example 50, further including a cannabinoid obtained as a distillate from *cannabis*, and a carrier system.

<51> A topical antibiotic including the formulation of Production Example 50, further including a cannabinoid obtained as an extract from *cannabis*, and a carrier system.

<52> A topical antibiotic including the formulation of Production Example 50, further including a cannabinoid obtained as a resin from *cannabis*, and a carrier system.

<53> A topical antibiotic including the formulation of Production Example 50, further including a cannabinoid isolate obtained from *cannabis*, and a carrier system.

<54> A topical antibiotic including the formulation of Production Example 50, further including a cannabinoid obtained from *Cannabis* indica, *Cannabis ruderalis*, or *Cannabis sativa*, and a carrier system.

<55> A topical antibiotic including the formulation of Production Example 50, further including a cannabinoid present as an oil from *cannabis*, and a carrier system.

<56> A topical antibiotic including the formulation of Production Example 50, further including a cannabinoid present as hempseed oil, and a carrier system.

<57> A topical antibiotic including the formulation of Production Example 50, further including a cannabinoid that is synthetically prepared, and a carrier system.

<58> A topical antibiotic including the formulation of Production Example 50, further including a cannabinoid that is at least one of THC (tetrahydrocannabinol), THCA (tetrahydrocannabinolic acid), CBD (cannabidiol), CBDA (cannabidiolic acid), CBN (cannabinol), CBG (cannabigerol), CBC (cannabichromene), CBL (cannabicyclol) CBV (cannabivarin), THCV (tetrahydrocannabivarin), CBDV (cannabidivarin), CBCV (cannabichromevarin), CBGV (cannabigerovarin), CBGM (cannabigerol monomethyl ether), CBE (cannabielsoin), and CBT (cannabicitran), and a carrier system.

<59> A topical antibiotic including the formulation of Production Example 50, further including a cannabinoid that is at least one of CBD and THC, and a carrier system.

<60> A topical antibiotic including the formulation of Production Example 50, further including a terpene, and a carrier system.

<61> A topical antibiotic including the formulation of Production Example 50, further including a terpene that is a sesquiterpene, and a carrier system.

<62> A topical antibiotic including the formulation of Production Example 50, further including a terpene obtained as a distillate from plant matter, and a carrier system.

<63> A topical antibiotic including the formulation of Production Example 50, further including a terpene obtained as an extract from plant matter, and a carrier system.

<64> A topical antibiotic including the formulation of Production Example 50, further including a terpene obtained as a resin from plant matter, and a carrier system.

<65> A topical antibiotic including the formulation of Production Example 50, further including a terpene obtained from *Cannabis sativa*, *Syzygium aromaticum* (cloves), rosemary, or hops, and a carrier system.

<66> A topical antibiotic including the formulation of Production Example 50, further including a terpene that is synthetically prepared, and a carrier system.

<67> A topical antibiotic including the formulation of Production Example 50, further including a terpene that is Beta-Caryophyllene, and a carrier system.

<68> A topical antibiotic including the formulation of Production Example 50, which is a topical first aid antibiotic.

<69> A topical antibiotic including the formulation of Production Example 50, further including at least one of light mineral oil, mineral oil, lanolin, aloe vera gel, lanolin, methylparaben, propylparaben, vitamin A palmitate, cethanol, squalane, purified lanolin, cetearyl alcohol, tocopheryl acetate, ethanol, vitamin E, water, glycerin, hydroxyethylcellulose, chlorhexidine gluconate, glucono delta lactone, sodium hydroxide, dipropylene glycol, dimethyl sulfoxide, sorbic acid, ascorbic acid (vitamin C), magnesium stearate, stearic acid, sodium bicarbonate, acetic acid, cholecalciferol (vitamin D3), dipropylene glycol, histidine, and diazolidinyl urea.

<70> A topical antibiotic including the formulation of Production Example 50, wherein the bacitracin is present in 500±100 units per gram.

<71> A topical antibiotic including the formulation of Production Example 50, wherein the bacitracin zinc is present in 500±100 units per gram.

<72> A topical antibiotic including the formulation of Production Example 50, wherein the neomycin sulfate is present in 5±1 mg per gram.

<73> A topical antibiotic including the formulation of Production Example 50, wherein the neomycin is present in 3.5±0.7 mg per gram.

<74> A topical antibiotic including the formulation of Production Example 50, wherein the tetracycline is present in 3±0.6 wt. %.

<75> A topical antibiotic including the formulation of Production Example 50, wherein the tetracycline hydrochloride is present in 3±0.6 wt. %.

<76> A topical antibiotic including the formulation of Production Example 50, wherein the polymyxin b sulfate is present in 5,000-10,000 units per gram.

<77> A topical antibiotic including the formulation of Production Example 50, that includes:
  (i) bacitracin, or
  (ii) bacitracin zinc, or
  (iii) neomycin sulfate, or
  (iv) tetracycline hydrochloride, or
  (v) polymyxin b sulfate, or
  (vi) bacitracin zinc and polymyxin b sulfate, or
  (vii) bacitracin zinc, neomycin sulfate, and polymyxin b sulfate.

<78> A topical antibiotic including the formulation of Production Example 50, that further includes at least one of lidocaine and pramoxine hydrochloride; which is a topical first aid antibiotic ointment with pain relief.

<79> A topical antibiotic including the formulation of Production Example 50, that further includes at least one of 4±1 wt. % lidocaine and 10±2 mg per gram pramoxine hydrochloride; which is a topical first aid antibiotic ointment with pain relief.

<80> The topical antibiotic of any one of the above embodiments, wherein the cannabinoid, terpene, flavonoid, or combination thereof, is present in an aggregate amount of up to 20 wt. %.

<81> The topical antibiotic of any one of the above embodiments, wherein the cannabinoid, terpene, flavonoid, or combination thereof, is present in an aggregate amount of up to 10 wt. %.

<82> The topical antibiotic of any one of the above embodiments, wherein the cannabinoid, terpene, flavonoid, or combination thereof, is present in an aggregate amount of up to 5 wt. %.

<83> The topical antibiotic of any one of the above embodiments, wherein the cannabinoid, terpene, flavonoid, or combination thereof, is present in an aggregate amount of up to 1 wt. %.

<84> The topical antibiotic of any one of the above embodiments, wherein the cannabinoid, terpene, flavonoid, or combination thereof, is present in an aggregate amount of up to 0.5 wt. %.

<85> The topical antibiotic of any one of the above embodiments, wherein the cannabinoid, terpene, flavonoid, or combination thereof, is present in an aggregate amount of 0.330±0.1 wt. %.

<86> The topical antibiotic of any one of the above embodiments, wherein the cannabinoid, terpene, flavonoid, or combination thereof, is present in an aggregate amount of 0.1 to 20 wt. %.

<87> The topical antibiotic of any one of the above embodiments, wherein the cannabinoid, terpene, flavonoid, or combination thereof, is present in an aggregate amount of 0.1 to 10 wt. %.

<88> The topical antibiotic of any one of the above embodiments, wherein the cannabinoid, terpene, flavonoid, or combination thereof, is present in an aggregate amount of 0.1 to 5 wt. %.

<89> The topical antibiotic of any one of the above embodiments, wherein the cannabinoid, terpene, flavonoid, or combination thereof, is present in an aggregate amount of 0.01 to 2.5 wt. %.

<90> The topical antibiotic of any one of the above embodiments, wherein the cannabinoid, terpene, flavonoid, or combination thereof, is present in an aggregate amount of 0.01 to 1 wt. %.

<91> The topical antibiotic of any one of the above embodiments, wherein the cannabinoid, terpene, flavonoid, or combination thereof, is present in an aggregate amount of 0.01 to 0.5 wt. %.

<92> The topical antibiotic of any one of the above embodiments, wherein the cannabinoid, terpene, flavonoid, or combination thereof, is present in an aggregate amount of 1 to 20 wt. %.

<93> The topical antibiotic of any one of the above embodiments, wherein the cannabinoid, terpene, flavonoid, or combination thereof, is present in an aggregate amount of 1 to 10 wt. %.

<94> The topical antibiotic of any one of the above embodiments, wherein the cannabinoid, terpene, flavonoid, or combination thereof, is present in an aggregate amount of 1 to 5 wt. %.

<95> The topical antibiotic of any one of the above embodiments, wherein the cannabinoid, terpene, flavonoid, or combination thereof, is present in an aggregate amount of 0.05 to 2.5 wt. %.

<96> The topical antibiotic of any one of the above embodiments, wherein the cannabinoid, terpene, flavonoid, or combination thereof, is present in an aggregate amount of 0.05 to 1 wt. %.

<97> The topical antibiotic of any one of the above embodiments, wherein the cannabinoid, terpene, flavonoid, or combination thereof, is present in an aggregate amount of 0.05 to 0.5 wt. %.

<98> The topical antibiotic of any one of the above embodiments, wherein the cannabinoid, terpene, flavonoid, or combination thereof, is CBD isolate, dissolved in hemp extract.

<99> The topical antibiotic of any one of the above embodiments, wherein the cannabinoid, terpene, flavonoid, or combination thereof, is CBD isolate, dissolved in 1±0.2 wt. % organic hemp extract.

<100> The topical antibiotic of any one of the above embodiments, wherein the cannabinoid, terpene, flavonoid, or combination thereof, is 1±0.75 wt. % CBD isolate, dissolved in hemp extract.

<101> The topical antibiotic of any one of the above embodiments, wherein the cannabinoid, terpene, flavonoid, or combination thereof, is 1±0.75 wt. % CBD isolate, dissolved in 1±0.2 wt. % organic hemp extract.

<102> The topical antibiotic of any one of the above embodiments, which is in the form of a gel, pump gel, gel packet, cream, lotion, roll-on liquid, roll-on gel, spray, pump spray, aerosol spray, stick, patch, ointment, liniment, or balm.

<103> A topical antibiotic including the formulation of Production Example 50, further including a cannabinoid, terpene, flavonoid, or combination thereof, and a carrier system; wherein the cannabinoid, terpene, flavonoid, or combination thereof, while present in the aggregate amounts, are characterized as inactive ingredients.

<104> A topical antibiotic including the formulation of Production Example 50, further including a cannabinoid, terpene, flavonoid, or combination thereof, and a carrier system; wherein the cannabinoid, terpene, flavonoid, or combination thereof, while present in the aggregate amounts, are characterized as an excipient.

<105> A topical antibiotic including the formulation of Production Example 50, further including a cannabinoid, terpene, flavonoid, or combination thereof, and a carrier system; wherein the cannabinoid, terpene, flavonoid, or combination thereof, while present in the aggregate amounts, are characterized as active ingredients.

<106> A topical antibiotic including the formulation of Production Example 50, further including a cannabinoid, terpene, flavonoid, or combination thereof, and a carrier system; wherein the cannabinoid, terpene, flavonoid, or combination thereof, while present in the aggregate amounts, are characterized as a first aid antibiotic.

<107> The topical antibiotic of any one of the above embodiments, which is in the form of a cream or ointment.

<108> The topical antibiotic of any one of embodiments <1> to <107>, having a total THC content of less than 0.05 mg/mL, wherein the total THC content is defined as the amount of THCA/mL*0.877, plus the amount of THC/mL*1, expressed as:

$$\text{Total THC content} = (\text{amount of THCA/mL} \ast 0.877) + (\text{amount of THC/mL} \ast 1) < 0.05 \text{ mg/mL}$$

<109> The topical antibiotic of any one of embodiments <1> to <107>, having a total THC content of less than 0.025 mg/mL, wherein the total THC content is defined as the amount of THCA/mL*0.877, plus the amount of THC/mL*1, expressed as:

$$\text{Total THC content} = (\text{amount of THCA/mL} \ast 0.877) + (\text{amount of THC/mL} \ast 1) < 0.025 \text{ mg/mL}$$

<110> The topical antibiotic of any one of embodiments <1> to <109>, substantially free from (a)-(e):
(a) Tetrahydrocannabinol (THC),
(b) Tetrahydrocannabinolic Acid (THCA),
(c) Cannabidiolic Acid (CBDA),
(d) Cannabinol (CBN),
(e) Cannabigerol (CBG),
such that any of (a) (e) present in the topical antibiotic is present such that the topical antibiotic includes each in no more than 0.01 mg/mL.

<111> The topical antibiotic of any one of embodiments <1> to <110>, substantially free from (a) (e):
(a) Tetrahydrocannabinol (THC),
(b) Tetrahydrocannabinolic Acid (THCA),
(c) Cannabidiolic Acid (CBDA),
(d) Cannabinol (CBN),
(e) Cannabigerol (CBG),
such any one or more of (a) (e) that is present in the topical antibiotic is present in a total amount of up to 0.02 mg/mL.

<112> A method that includes topically administering to a subject the topical antibiotic of any one of the above embodiments.

<113> A method of first aid to help prevent infection in at least one of minor cuts, scrapes, and burns, the method includes topically administering to the affected areas of a subject in need thereof the topical antibiotic of any one of embodiments <1> to <111>.

<114> A method of first aid to help prevent infection and for the temporary relief of pain or discomfort due to at least one of minor cuts, scrapes, and burns, the method includes topically administering to the affected areas of a subject in need thereof the topical antibiotic of any one of embodiments <1> to <111>.

<115> The method of any one of embodiments <111> to <114>, further including cleaning the affected areas prior to topically administering the topical antibiotic to the affected areas.

<116> The method of any one of embodiments <111> to <115>, wherein the topical antibiotic is administered to the affected areas 1 to 3 times daily.

<117> The method of any one of embodiments <111> to <116>, further including after the topical antibiotic is administered to the affected areas, covering the affected areas with a sterile bandage.

<118> The method of any one of embodiments <111> to <117>, wherein the subject is at least 2 years old.

What is claimed is:

1. A method of first aid to prevent bacterial infection due to at least one of minor cuts, scrapes, and burns, the method comprising topically administering to affected areas of a subject in need thereof a topical antibiotic ointment comprising:
   (a) bacitracin zinc;
   (b) cannabidiol (CBD); and
   (c) petrolatum;
wherein the CBD is present as a CBD isolate, dissolved or dispersed in hemp extract.

2. The method of claim 1, wherein the topical antibiotic ointment further comprises lidocaine or pramoxine hydrochloride.

3. The method of claim 1, further comprising after the topical antibiotic ointment is administered to the affected areas, covering the affected areas with a sterile bandage.

4. The method of claim 1, wherein the topical antibiotic ointment further comprises at least one compound selected from the group consisting of mineral oil, lanolin, aloe vera gel, methylparaben, propylparaben, vitamin A palmitate, squalane, cetearyl alcohol, tocopheryl acetate, ethanol, vitamin E, water, glycerin, hydroxyethylcellulose, chlorhexidine gluconate, glucono delta lactone, sodium hydroxide, dipropylene glycol, dimethyl sulfoxide, sorbic acid, ascorbic acid (vitamin C), magnesium stearate, stearic acid, sodium bicarbonate, acetic acid, cholecalciferol (vitamin D3), dipropylene glycol, histidine, and diazolidinyl urea.

5. The method of claim 1, wherein the bacitracin zinc is present in 500±100 units per gram of the topical antibiotic ointment.

6. The method of claim 1, wherein the CBD isolate is present in the topical antibiotic ointment in 1±0.75 wt. %.

7. The method of claim 1, wherein the hemp extract is organic hemp extract, present in the topical antibiotic ointment in 1±0.2 wt. %.

8. The method of claim 1, wherein the topical antibiotic ointment has a total Tetrahydrocannabinol (THC) content of less than 0.02 mg/mL.

9. The method of claim 1, wherein the topical antibiotic ointment is substantially free from (a)-(e):
  (a) Tetrahydrocannabinol (THC),
  (b) Tetrahydrocannabinolic Acid (THCA),
  (c) Cannabidiolic Acid (CBDA),
  (d) Cannabinol (CBN), and
  (e) Cannabigerol (CBG), such that any of (a)-(e) present in the topical antibiotic ointment is present such that the topical antibiotic ointment includes each in no more than 0.01 mg/mL.

10. A method of first aid to prevent bacterial infection due to at least one of minor cuts, scrapes, and burns, the method comprising topically administering to affected areas of a subject in need thereof a topical antibiotic ointment comprising:
  (a) bacitracin zinc;
  (b) cannabidiol (CBD);
  (c) petrolatum; and
  (d) glycerin;

wherein the CBD is present as a CBD isolate, dissolved or dispersed in hemp extract;

and wherein the bacitracin zinc is present in 500±100 units per gram of the topical antibiotic ointment.

11. The method of claim 10, wherein the topical antibiotic ointment has a total THC content of less than 0.02 mg/mL.

12. The method of claim 10, wherein the topical antibiotic ointment is substantially free from (a)-(e):
  (a) Tetrahydrocannabinol (THC),
  (b) Tetrahydrocannabinolic Acid (THCA),
  (c) Cannabidiolic Acid (CBDA),
  (d) Cannabinol (CBN), and
  (e) Cannabigerol (CBG), such that any of (a)-(e) present in the topical antibiotic ointment is present such that the topical antibiotic ointment includes each in no more than 0.01 mg/mL.

13. The method of claim 10, wherein the hemp extract is organic hemp extract, present in the topical antibiotic ointment in 1±0.2 wt. %.

* * * * *